(12) United States Patent
Fujii et al.

(10) Patent No.: US 10,209,506 B2
(45) Date of Patent: Feb. 19, 2019

(54) LIGHT SOURCE OPTICAL SYSTEM HAVING TAPERED LIGHT GUIDE ROD

(71) Applicant: HOYA CORPORATION, Tokyo (JP)

(72) Inventors: Hiroaki Fujii, Tokyo (JP); Sachiko Nasu, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 128 days.

(21) Appl. No.: 15/106,993

(22) PCT Filed: Mar. 23, 2016

(86) PCT No.: PCT/JP2016/001670
§ 371 (c)(1),
(2) Date: Jun. 21, 2016

(87) PCT Pub. No.: WO2016/152153
PCT Pub. Date: Sep. 29, 2016

(65) Prior Publication Data
US 2017/0115478 A1    Apr. 27, 2017

(30) Foreign Application Priority Data
Mar. 24, 2015 (JP) .................... 2015-060316

(51) Int. Cl.
*G02B 6/26* (2006.01)
*G02B 23/24* (2006.01)
(Continued)

(52) U.S. Cl.
CPC .......... *G02B 23/2469* (2013.01); *A61B 1/002* (2013.01); *A61B 1/0669* (2013.01);
(Continued)

(58) Field of Classification Search
CPC ...... G02B 6/264; G02B 6/262; G02B 6/0008; A61B 1/0669; A61B 1/07; F21V 33/0068; F21V 2200/13; F21W 2131/20
See application file for complete search history.

(56) References Cited

U.S. PATENT DOCUMENTS 3,437,804 A * 4/1969 Schaefer ............. G02B 6/4206
                                                         313/113
3,583,795 A    6/1971 Heine
(Continued)

FOREIGN PATENT DOCUMENTS

| JP | S63-249811 | 10/1988 |
| JP | 6-22811 | 6/1994 |

(Continued)

OTHER PUBLICATIONS

Search Report issued in WIPO Patent Application No. PCT/JP2016/001670, dated Oct. 5, 2017.
(Continued)

*Primary Examiner* — Ismael Negron
(74) *Attorney, Agent, or Firm* — Greenblum & Bernstein, P.L.C.

(57) ABSTRACT

A light source optical system includes a light source, an optical system that collects light incident from the light source; and a light guide rod having a reflecting inner surface for guiding light received through an entrance port to an exit port by total internal reflection, the reflecting inner surface being gradually tapered, towards a light guide axis in the direction of the exit port, in one of an entire region defined from the entrance port to the exit port, and a region defined from a midway point between the entrance port and the exit port to the exit port.

7 Claims, 9 Drawing Sheets

(51) Int. Cl.
*G02B 6/32* (2006.01)
*G02B 6/00* (2006.01)
*A61B 1/06* (2006.01)
*A61B 1/07* (2006.01)
*A61B 1/002* (2006.01)
*F21V 8/00* (2006.01)

(52) U.S. Cl.
CPC ................ *A61B 1/07* (2013.01); *G02B 6/00* (2013.01); *G02B 6/0006* (2013.01); *G02B 6/32* (2013.01); *G02B 23/2461* (2013.01)

(56) References Cited

U.S. PATENT DOCUMENTS

| | | | | |
|---|---|---|---|---|
| 4,936,668 A * | 6/1990 | Mori | ............... | A61N 5/06 385/31 |
| 5,522,006 A | 5/1996 | Takeuchi et al. | | |
| 5,727,108 A * | 3/1998 | Hed | ............... | G02B 6/0008 362/576 |
| 5,810,469 A * | 9/1998 | Weinreich | ............... | F21V 7/09 362/298 |
| 5,860,723 A * | 1/1999 | Domas | ............... | F21V 29/004 362/294 |
| 5,888,194 A | 3/1999 | Utsumi et al. | | |
| 6,850,095 B2 * | 2/2005 | Sayers | ............... | F21S 48/1154 359/726 |
| 7,127,141 B2 * | 10/2006 | Fein | ............... | G02B 6/102 385/39 |
| 7,543,959 B2 * | 6/2009 | Bierhuizen | ............... | H04N 9/315 257/98 |
| 8,864,328 B2 * | 10/2014 | Toyota | ............... | G02B 6/0008 362/511 |
| 2005/0276050 A1 * | 12/2005 | Pate | ............... | G02B 17/0605 362/261 |
| 2006/0222298 A1 | 10/2006 | Hatori | | |
| 2008/0049196 A1 * | 2/2008 | Wang | ............... | G03B 21/208 353/98 |
| 2008/0055923 A1 * | 3/2008 | Miller | ............... | G02B 6/0008 362/580 |
| 2010/0002202 A1 * | 1/2010 | Dierks | ............... | G02B 6/0008 353/85 |

FOREIGN PATENT DOCUMENTS

| | | |
|---|---|---|
| JP | 6-43772 | 11/1994 |
| JP | 2002-333533 | 11/2002 |
| WO | 2013/140961 A1 | 9/2013 |

OTHER PUBLICATIONS

Extended European Search Report issued for European Patent Application No. 16727277.2 dated Oct. 26, 2018.

* cited by examiner

LIGHT SOURCE OPTICAL SYSTEM HAVING TAPERED LIGHT GUIDE ROD

TECHNICAL FIELD

The present invention relates to a light source optical system and a light source device.

BACKGROUND ART

Endoscope systems for observing a body cavity of a patient are known. In general, an endoscope system is provided with a light source optical system for illuminating a body cavity of a patient. A concrete configuration of the light source optical system of this type is described, for example, in Japanese Patent Provisional Publication No. 2002-333533A (hereafter, referred to as patent document 1).

The light source optical system described in the patent document 1 includes a light source side lens (a convex lens or a ball lens) for letting light emitted from a light source enter a light guide. The light guide is an optical fiber including a core part and a clad part, and is configured such that the core diameter thereof is enlarged in a cone shape on an entrance end face side. Since, in the patent document 1, the area of an entrance end face of the light guide is large, a large amount of light can be taken in the light guide and thereby the inside of a body cavity can be illuminated brightly.

SUMMARY OF INVENTION

Regarding manufacturing of the light guide, the patent document 1 describes that, in consideration of a condition during a process for fiber forming from optical fiber base material in which the outer diameter of a lower end portion of the optical fiber base material gradually gets smaller until the outer diameter becomes a predetermined fiber diameter and then a portion having the predetermined outer diameter continues, a fiber portion extending downward is cut out to include the conical shape part at the lower portion of the base material. However, the patent document 1 does not describe how the light guide is manufactured in order to precisely control the size of the diameter of the lower portion (an entrance end face side) of the optical fiber base material. In general, it is difficult to mass-produce a light guide having this type of particular shape. Therefore, it is thought that the manufacturing yield of the light guide described in the patent document 1 is low.

The present invention is made in view of the above described circumstances. That is, the object of the present invention is to provide a light source optical system and a light source device including a light guide configured such that an area of an entrance port (an entrance face end disposed on a light source side) is larger than an area of an exit port, while achieving easy manufacturing.

According to an aspect of the invention, there is provided a light source optical system, comprising: a collecting optical system that collects light incident on the collecting optical system from a light source, the collecting optical system having at least one lens; and a light guide rod having an entrance port through which the light collected by the collecting optical system enters the light guide rod, an reflecting inner surface defining a light guide path for the light inputted through the entrance port, and an exit port through which the light guided in the light guide path by being totally reflected on the reflecting inner surface exits. In this configuration, the reflecting inner surface includes a taper part formed in one of an entire region defined from the entrance port to the exit port and a part defined from a midway point between the entrance port and the exit port to the exit port, the taper part being inclined to gradually get closer to an axis line of the light guide path at a point closer to the exit port.

According to the above described configuration, it is possible to provide a light source optical system and a light source device including a light guide configured such that an area of an entrance port (an entrance face end disposed on a light source side) is larger than an area of an exit port, while achieving easy manufacturing.

In at least one aspect, an area of the exit port may be smaller than an area of the entrance port.

In at least one aspect, the light guide rod may be configured such that an area of the light guide rod defined, in a plane perpendicularly intersecting with the axis line of the light guide path, in an entire of the light guide path from the entrance port to the exit port becomes smallest at the exit port.

In at least one aspect, each of the entrance port and the exit port may be circular. In this case, when a diameter of the entrance port is defined as $D_{EN}$ (unit: mm) and a diameter of the exit port is defined as $D_{EX}$ (unit: mm), the light guide rod may satisfy a following condition:

$$1.5 \leq D_{EN}/D_{EX} \leq 3.0.$$

In at least one aspect, when a length of the taper part in a direction of the axis line is defined as L (unit: mm), the light guide rod may satisfy a following condition:

$$0.03 \leq D_{EN}/L \leq 0.16.$$

In at least one aspect, the light guide rod may satisfy a following condition:

$$10 \leq D_{EX}/D_{EN} \times L \leq 60.$$

In at least one aspect, the light guide rod may satisfy a following condition:

$$1000 \leq D_{EX}/D_{EN} \times L^2 \leq 4000.$$

In at least one aspect, when a numerical aperture of the collecting optical system is defined as NA1, the light source optical system may satisfy a following condition:

$$0.7 \leq D_{EN}/D_{EX} \times NA1 \leq 1.5.$$

In at least one aspect, when a distance between a lens surface closest to the light guide rod in the collecting optical system and the entrance port of the light guide rod is defined as Bf (unit: mm), an effective diameter of the lens surface is defined as phi (unit: mm), and (Bf/phi) is defined as NA2, the light source optical system may satisfy a following condition:

$$0.7 \leq D_{EN}/D_{EX} \times NA2 \leq 1.5.$$

In at least one aspect, when a diameter of an entrance end face of a light guide on which the light emerging from the exit port of the light guide rod is incident is defined as $D_L$ (unit: mm), the light guide rod satisfy a following condition:

$$D_L < D_{EX}.$$

In at least one aspect, the reflecting inner surface may be configured such that the taper part has a taper shape being inclined linearly or nonlinearly to get gradually closer to the axis line of the light guide path.

In at least one aspect, the collecting optical system may converge the light incident on the collecting optical system from the light source in a vicinity of the entrance port of the light guide rod.

According to another aspect of the invention, there is provided a light source device, comprising: a light source emitting light; and one of the above described light source optical systems. In this configuration, the light emitted from the light source is incident on the light source optical system.

DESCRIPTION OF EMBODIMENTS

Hereinafter, an embodiment of the present invention is described with reference to the accompanying drawings. In the following, an electronic endoscope system is explained as an embodiment of the invention by way of example.
(Configuration of Electronic Endoscope System 1)

Figure 1:
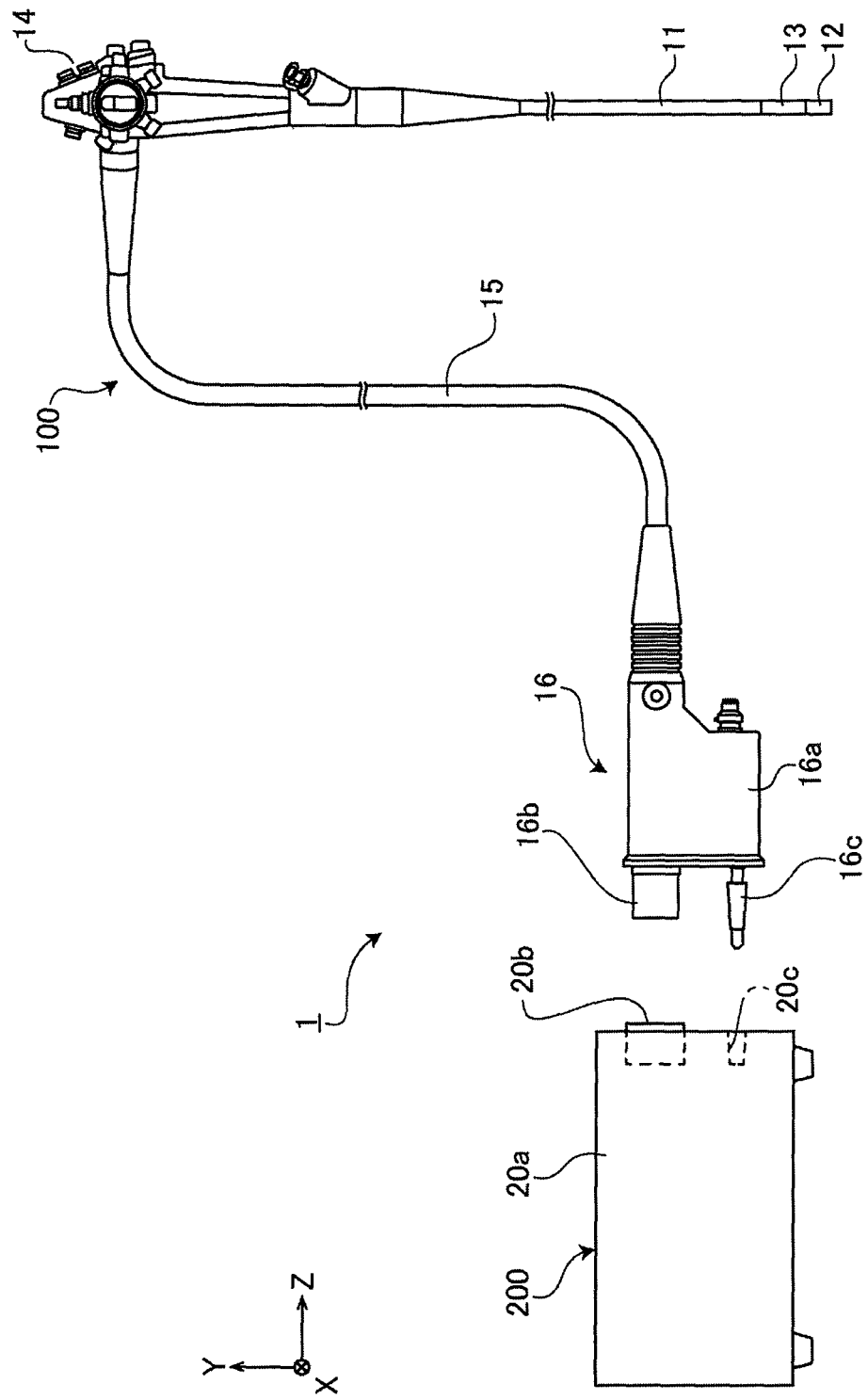
FIG. 1 illustrates an outer appearance of an electronic endoscope system according to an embodiment of the invention.

FIG. 1 illustrates an outer appearance of an electronic endoscope system 1 according to an embodiment. As shown in FIG. 1, the electronic endoscope system 1 includes an electronic scope 100 and a processor 200. In FIG. 1, a direction perpendicular to a paper face of FIG. 1 is defined as X-direction, and two directions which are parallel with the paper face of FIG. 1 and perpendicularly intersecting with the X-axis are defined as Y-direction and Z-direction. Y-direction is the vertical direction (i.e., a direction of a gravitational line), and X-direction and Z-direction are horizontal directions perpendicular to the vertical direction. These definitions of X, Y and Z directions are also applied to the other drawings.

As shown in FIG. 1, the electronic scope 100 includes a flexible insertion tube 11 covered with a flexible sheath. A tip portion (a bending part 13) of the flexible insertion tube 11 bends in response to a remote operation from a hand operation part 14 connected to a proximal end of the flexible insertion tube 11. A bending mechanism may be a known mechanism installed in a general endoscope, and is configured to bend the bending part 13 by drawing motion of an operation wire in conjunction with a rotation operation to a bending operation knob of the hand operation part 14. To a tip of the bending part 13, a proximal end of a tip part 12 covered with a resin housing having rigidity is connected. The direction of the tip part 12 changes in accordance with bending motion by a rotation operation to the bending operation knob, and thereby an imaging area by the electronic endoscope 100 also changes. Furthermore, a universal cable 15 extends from the hand operation part 14, and a connector part 16 is connected to a proximal end of the universal cable 15.

The connector part 16 includes a connector case 16a formed of synthetic resins having rigidity. The connector case 16a is formed of a front side case and a back side case having substantially symmetric shapes. The connector case 16a accommodates and holds various components, such as an electronic circuit board, in a closed space defined by letting the front side case and the back side case be fitted to each other so as to protect the various components from external shock. The connector case 16a holds an electric connection plug 16b and an optical connection plug 16c.

The processor 200 is configured as an integrated device in which a light source device and components for image signal processing are integrally provided. On a front panel surface of a housing 20a of the processor 200, a connector part is provided. The connector part includes an electric connection jack 20b and an optical connection jack 20c. The electric connection jack 20b is electrically connected to the components for the image signal processing in the processor 200, and the optical connection jack 20c is optically connected to the light source provided in the processor 200.

The electric connection jack 20b has a connection structure corresponding to the electric connection plug 16b, and the optical connection jack 20c has a connection structure corresponding to the optical connection plug 16c. By connecting the electric connection plug 16b and the optical connection plug 16c to the electric connection jack 20b and the optical connection jack 20c, respectively, the electronic scope 100 and the processor 200 are connected electrically and optically.
(Configuration of Light Source Device 250)

Figure 2:
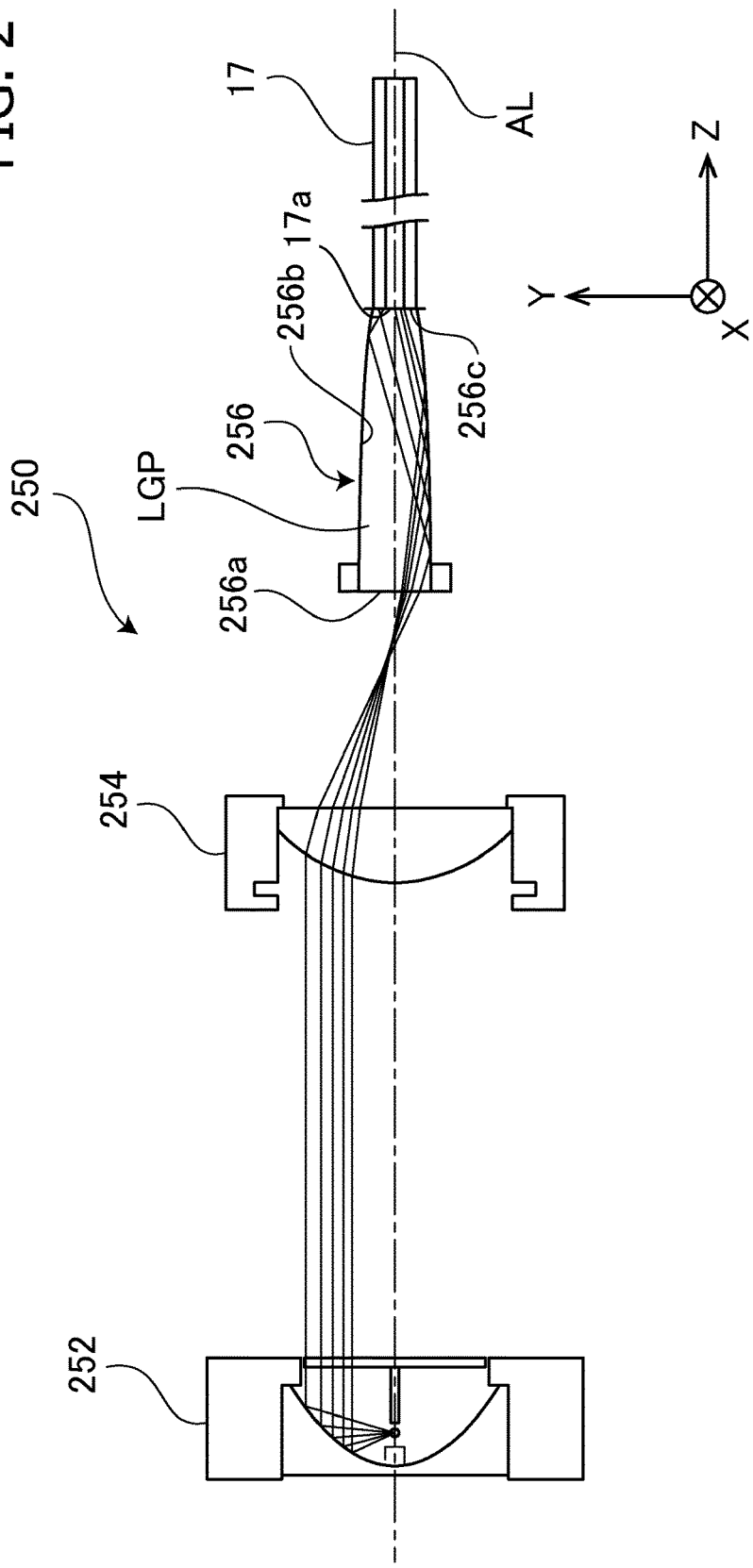
FIG. 2 illustrates a configuration of a light source device installed in a housing of a processor provided in the electronic endoscope system according to the embodiment.

FIG. 2 illustrates a configuration of a light source device 250 installed in the housing 20a of the processor 200 according to the embodiment. In FIG. 2, for convenience of explanation, components of the light source device 250 are shown as a side cross section.

As shown in FIG. 2, the light source device 250 includes a light source 252, a collecting optical system 254 and a light guide rod 256.

The light source 252 is an arc lamp, and specifically is a xenon short arc lamp having a reflector for emitting a substantially collimated white light beam. It should be noted that, in another embodiment, the light source 252 may be a high intensity lamp, such as a halogen lamp, a mercury lamp or a metal-halide lamp, or an LED (Light Emitting Diode).

The substantially collimated light beam emitted from the light source 252 is incident on the collecting optical system 254. The collecting optical system 254 includes at least one lens (one lens in the example in FIG. 2). The substantially collimated light beam entered the collecting optical system 254 is collected by the collecting optical system 254, is converged in the vicinity of an entrance port 256a (an end face on a light source 252 side) of the light guide rod 256, and enters the inside of the light guide rod 256. Positioning of the collecting optical system 254 and the light guide rod 256 is easily, because the entrance port 256a of the light guide rod 256 may be placed at a converging point of the collecting optical system 254.

The light guide rod 256 is an optical rod having the light guiding function, and is, for example, a single rod or a glass rod. The single rod is a rod having at least a double structure of a core and a clad. The glass rod is a rod not having a clad. In the inside of the light guide rod 256, a reflecting inner surface 256b defining a light guide path LOP for the light entered from the entrance port 256a is formed. As shown in FIG. 2, the light entered the inside of the light guide path LOP is guided in the inside of the light guide path LGP by being totally reflected by the reflecting inner surface 256b, and is emitted from an exit port 256c (an end face on an electronic scope 100 side).

The light emitted from the exit port 256c is collected at an entrance end face 17a of an LCB (Light Carrying Bundle) 17 provided in the optical connection plug 16c. The illumination light entered the inside of the LCB 17 propagates through the inside of the LCB 17, and is emitted from an exit end face of the LCB 17 positioned in the tip part 12. Then, the illumination light emitted from the LCB 17 illuminates a subject via a light distribution lens (not shown).

(Details about Light Guide Rod 256)

Hereafter, the light source device 250 according to the embodiment is explained in detail. In the following, explanation is given while focusing on the configuration of the light guide rod 256.

The reflecting inner surface 256b of the light guide rod 256 is configured such that the entire reflecting inner surface 256b or a part of the reflecting inner surface 256b expanding from a midway position to the exit port 256c is formed as a taper part inclined to approach an axis line AL (a center axis line) of the light guide path (the light guide rod 256) at a point closer to the exit port 256c. In this embodiment, the tapered part has a linear taper shape; however, in another embodiment, the taper part may have a nonlinear taper shape (e.g., an exponential function taper shape or a parabolic taper shape). For convenience of explanation, the configuration in which the entire reflecting inner surface 256b expanding from the entrance port 256a to the exit port 256c is formed as a taper part is referred to as an "overall taper configuration", and the configuration in which a part of the reflecting inner surface 256b expanding from a midway position to the exit port 256c is formed as a taper part is referred to as a "partial taper configuration".

In the case of the overall taper configuration, the entire reflecting inner surface 256b expanding from the entrance port 256a to the exit port 256c is inclined to gradually approach the axis line AL at a point closer to the exit port 256c. Therefore, the light guide path LGP is formed in a shape of a frustum where the entrance port 256a and the exit port 256c are defined as parallel surfaces of the frustum. Furthermore, the reflecting inner surface 256b is configured such that an area defined in a plane perpendicularly intersecting with the axis line AL gets gradually smaller at a point closer to the exit port 256c. Furthermore, an area of the exit port 256c is smaller than an area of the entrance port 256a, and regarding an area defined in a plane perpendicularly intersecting with the axis line AL, the area of the exit port 256c is smallest in the entire light guide path LGP expanding from the entrance port 256a to the exit port 256c.

In the case of the partial taper configuration, the reflecting inner surface 256b is configured such that a part of the reflecting inner surface 256b expanding from the entrance port 256a to a midway position is parallel with the axis line AL, and a part expanding from the midway position to the exit port 256c is inclined to gradually get closer to the axis line AL. Therefore, the light guide path LGP is formed such that the part expanding from the entrance port 256a to the midway position is formed to have a shape of a cylinder, and the part expanding from the midway position to the exit port 256c is formed to have a shape of a frustum. Regarding an area defined in a plane perpendicularly intersecting with the axis line AL, the area of the light guide path LOP is constant in the part expanding from the entrance port 256a to the midway position, and gets smaller at a point closer to the exit port 256c in the part expanding from the midway position to the exit port 256c. Therefore, the area of the exit port 256c is smaller than the area of the entrance port 256a, and regarding an area defined in a plane perpendicularly intersecting with the axis line AL, the area of the exit port 256c is smallest in the entire light guide path LGP expending from the entrance port 256a to the exit port 256c.

In each of the overall taper configuration and the partial taper configuration, the taper part of the light guide rod 256 is inclined to gradually get closer to the axis line AL. Therefore, a light ray which has entered the inside of the light guide path LGP through the entrance port 256a at a first angle is emitted from the exit port 256c at a second angle which is larger than the first angle, and then illuminates the subject via the LCB 17 and the light distribution lens. That is, since a light ray having a lager NA (Numerical Aperture) enters the inside of the LCB 17, a light distribution angle of the illumination light emitted from the light distribution lens can be expanded, and thereby an illumination range for the subject by the illumination light can be expanded. In another point of view, the light guide rod 256 bears a part of the power which the collecting optical system 254 should have. Therefore, a degree of design freedom for the collecting optical system 254 can be enhanced. As an example, the collecting optical system 254 may be designed to have a long focus length. In such a case, since a wide space can be secured between the collecting optical system 254 and the light guide rod 256, it becomes possible to dispose components, such as an aperture stop, in the space between the collecting optical system 254 and the light guide rod 256, for example.

Since the light ray propagates through the light guide path LGP while repeating reflection in the light guide path LGP, distribution of the illumination light (the light intensity distribution) and spectrum of the illumination light can be uniformed. Therefore, even when the light guide rod 256 and the LCB 17 are disposed with a positional error in a plane perpendicular to the axis line AL, the intensity distribution and the spectrum of the illumination light can be prevented from being substantially changed due to the positional error.

Furthermore, when the collecting optical system 254 and the light guide rod 256 are disposed with a positional error, the light converging point by the collecting optical system 254 may shift with respect to the entrance port 256a. However, according to the embodiment, since the area of the entrance port 256a is large, the light convergence point adequately falls within the entrance port 256a. As a result, coupling loss of light can be avoided.

Since the light guide rod 256 is an optical rod having a simple structure in which at least a part is formed to be a taper part, it is not difficult to mass-produce the light guide rod 256 with high quality. That is, decrease of the manufacturing yield can be avoided.

Furthermore, there is no necessity to prepare an electronic scope having a special light guide shape shown in the patent document 1. That is, according to the embodiment, an electronic endoscope system can be configured using a genera-purpose electronic scope. Therefore, cost can be suppressed.

The entrance port 256a and the exit port 256c may be circular or rectangular, and may be similar to each other (e.g., the entrance port 256a and the exit port 256c are both circular) or may not be similar to each other (e.g., one of the entrance port 256a and the exit port 256c is circular and the other of the entrance port 256a and the exit port 256c is rectangular). Conditions described below are defined n the premise that each of the entrance port 256a and the exit port 256c is circular.

When a diameter of the entrance port 256a is defined as $D_{EN}$ (unit: mm) and a diameter of the exit port 256c is defined as $D_{EX}$ (unit: mm), the light guide rod 256 may be configured to satisfy the following condition (1):

$$1.5 \leq D_{EN}/D_{EX} \leq 30 \tag{1}$$

The condition (1) defines a ratio between diameters of the entrance port 256a and the exit port 256c of the light guide rod 256. By satisfying the condition (1), the taper part of the light guide rod 256 has an appropriate inclined angle with respect to the axis line AL. As a result, since a light ray having a larger angle and a larger NA is incident on the LCB 17, the light distribution angle of the illumination light emitted from the light distribution lens is expanded, and thereby the light distribution range for the subject by the illumination light can be further expanded. Furthermore, since the light ray propagates through the inside of the light guide path LOP while repeating reflection for appropriate times, the distribution and the spectrum of the illumination light can be further uniformed.

When the intermediate term of the condition (1) gets larger than the upper limit of the condition (1), the inclined angle of the taper part with respect to the axis line AL becomes too large, and thereby the loss of light amount when the light ray reflects in the light guide path LOP becomes large. In this case, it becomes difficult to illuminate the subject brightly. Furthermore, in this case, NA of light incident on the LCB 17 exceeds an entrance end face side NA (for example, which is, in general, approximately generally 0.6 to 0.8) of the LCB 17. Therefore, the light coupling loss between the light guide rod 256 and the LCB 17 becomes large. Furthermore, the entrance port 256a has a diameter which exceeds three-fold of the diameter of the exit port 256c which is defined depending on the diameter of the LCB 17. In this case, the entrance port 256a becomes too large, and therefore the ratio of light rays reaching the reflecting inner surface 256b in the light guide path LOP decreases. In this case, the advantageous effect of uniformization of the distribution and the spectrum of the illumination light by repeating of reflection cannot be attained adequately.

When the intermediate term of the condition (1) gets smaller than the lower limit of the condition (1), the inclined angle of the taper part with respect to the axis line AL becomes too small, and thereby the angle of the light ray emitted from the exit port 256c does not become adequately large. Therefore, in this case, the advantageous effect of expanding of the light distribution angle cannot be attained adequately.

When the length of the taper part in the direction of the axis line AL is defined as L (unit: mm), the light guide rod 256 may be configured to satisfy the following condition (2):

$$0.03 \leq D_{EN}/L \leq 0.16 \tag{2}$$

The condition (2) defines a ratio between the length of the taper part and the diameter of the entrance port 256a of the light guide rod 256. By satisfying the condition (2), the taper part has a more appropriate inclined angle with respect to the axis line AL, and thereby the advantageous effect of uniformization of the distribution and the spectrum of the illumination light is further enhanced and the loss of light amount when the light ray reflects in the light guide path LGP can be further suppressed.

When the intermediate term of the condition (2) gets larger than the upper limit of the condition (2), the entrance port 256a becomes too large, and thereby the ratio of light rays reaching the reflecting inner surface 256b in the light guide path LGP becomes small. In this case, the advantageous effect of uniformization of the distribution and the spectrum of the illumination light by repeating of reflection cannot be attained adequately.

When the intermediate term of the condition (2) gets smaller than the lower limit of the condition (2), the light ray reflects in the light guide path LGP a plurality of times, and thereby the loss of light amount by reflection becomes too large. As a result, it becomes difficult to illuminate the subject brightly. Furthermore, an NA of light incident on the LCB 17 exceeds the entrance end face side NA (for example, which is, in general, approximately generally 0.6 to 0.8) of the LCB 17. Therefore, coupling loss of light between the light guide rod 256 and the LCB 17 becomes large.

The light guide rod 256 may be configured to satisfy at least one of the following conditions (3) and (4):

$$10 \leq D_{EX}/D_{EN} \times L \leq 60 \tag{3}$$

$$1000 \leq D_{EX}/D_{EN} \times L^2 \leq 4000 \tag{4}$$

The conditions (3) and (4) define relationship between the length of the taper part and the ratio between the diameters of the entrance port 256a and the exit port 256c of the light guide rod 256. By satisfying the condition (3) or the condition (4), the light guide rod 256 has an appropriate shape (a shape attaining a low degree of light coupling loss between the collecting optical system 254 and the light guide rod 256) according to the NA of the collecting optical system 254.

When the intermediate term of the condition (3) gets larger than the upper limit of the condition (3) or the intermediate term of the condition (4) gets larger than the upper limit of the condition (4), the loss of light amount by reflection becomes too large because the light ray reflects in the light guide path LGP a plurality of times, and thereby it becomes difficult to illuminate the subject brightly. Furthermore, an NA of light incident on the LCB 17 exceeds the entrance end face side NA (for example, which is, in general, approximately generally 0.6 to 0.8) of the LCB 17. Therefore, coupling loss of light between the light guide rod 256 and the LCB 17 becomes large.

When the intermediate term of the condition (3) gets smaller than the lower limit of the condition (3) or the intermediate term of the condition (4) gets smaller than the lower limit of the condition (4), the number of reflections of the light ray in the light guide path LGP becomes too small. In this case, the advantageous effect of uniformization of the distribution and the spectrum of the illumination light by repeating of refection cannot be attained adequately.

When the NA (Numerical Number) of the collecting optical system 254 is defined as NA1, the light guide rod 256 may be configured to satisfy the following condition (5):

$$0.7 \leq D_{EN}/D_{EX} \times NA1 \leq 1.5 \tag{5}$$

The condition (5) defines relationship between the NA of the collecting optical system 254 and the ratio of diameters between the entrance port 256a and the exit port 256c. By satisfying the condition (5), the light guide rod 256 has an appropriate shape (a shape attaining a low degree of coupling loss of light between the collecting optical system 254 and the light guide rod 256) according to the NA of the collecting optical system 254. Furthermore, the advantageous effect of uniformization of the distribution and the spectrum of the illumination light is further enhanced.

When the intermediate term of the condition (5) gets larger than the upper limit of the condition (5), the ratio between the diameters of the incident entrance 256a and the exit entrance 256c becomes large with respect to the NA of the collecting optical system 254. Therefore, the loss of light amount when the light ray reflects in the light guide path LGP becomes large, and thereby it becomes difficult to illuminate the subject brightly. Furthermore, an NA of light incident on the LCB 17 exceeds the entrance end face side NA (for example, which is, in general, approximately generally 0.6 to 0.8) of the LCB 17. Therefore, coupling loss of light between the light guide rod 256 and the LCB 17 becomes large.

When the intermediate term of the condition (5) gets smaller than the lower limit of the condition (5), the angle of the light ray emitted from the exit port 256 does not become adequately large. Therefore, the advantageous effect of expanding of the light distribution angle cannot be attained adequately. Furthermore, since the NA of the collecting optical system 254 is too small, the focusing spot becomes large. In this case, it becomes impossible to let the light guide path LGP to take in an adequate amount of light through the entrance port 256a, and thereby loss of light amount becomes large.

When the spherical aberration of the collecting optical system 254 is suitably corrected, for example, by an aspherical surface lens, a condition defined directly by an NA by paraxial calculation (i.e., the condition (5)) can be used. However, when the spherical aberration of the collecting optical system 254 is large, it is preferable that the condition (5) is replaced with the following condition (6). That is, it is preferable that, when a distance between the entrance port 256a and a lens surface closest to the light guide rod 256 in the collecting optical system 256 is defined as Bf (unit: mm), and a diameter (i.e., an effective diameter) of the lens surface closest to the light guide rod 256 in the collecting optical system 256 is defined as phi (unit: mm), and (Bf/phi) is defined as NA2, the light guide rod 256 may satisfy the condition (6):

$$0.7 \leq D_{EN}/D_{EX} \times NA2 \leq 1.5 \quad (6).$$

When a diameter (a diameter of an entrance port) of an entrance end face 17a of the LCB 17 on which the light emerging from the exit port 256c is incident is defined as $D_L$ (unit: mm), the light guide rod 256 may satisfy the following condition (7):

$$D_L < D_{EX} \quad (7).$$

The condition (7) defines relationship between the exit port 256c of the light guide rod 256 and the entrance end face 17a of the LCB 17. By satisfying the condition (7), the coupling loss of light between the light guide rod 256 and the LCB 17 can be suppressed.

In the following, seven concrete numerical examples of the light source device 250 will be explained.

Example 1

Figure 3:
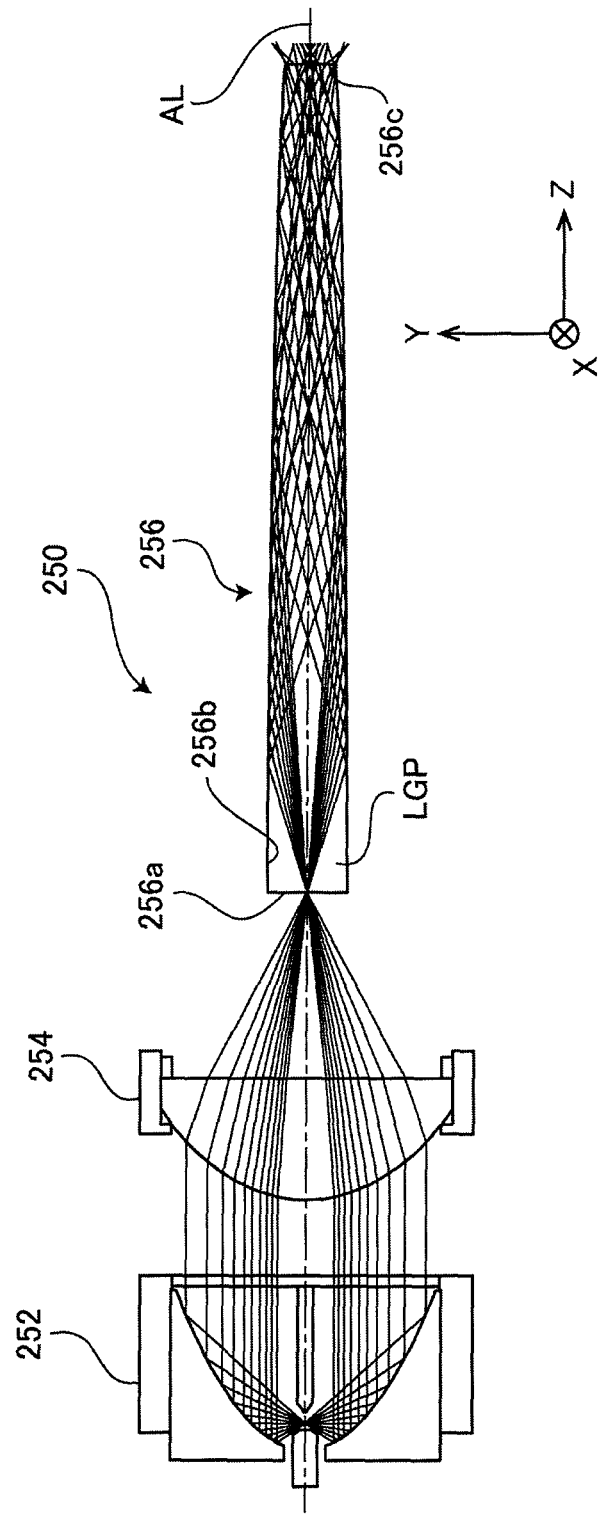
FIG. 3 illustrates a configuration of a light source device according to an example 1 of the invention.

FIG. 3 illustrates a configuration of the light source device 250 according to an example 1 of the invention. As shown in FIG. 3, in the example 1, the collecting optical system 254 has a single lens configuration. The numeric Table 1 described below shows concrete numeric data of the collecting optical system 254 according to the example 1.

TABLE 1

Unit: mm

Surface Data

| NO | R | D | N(D) | VD |
|---|---|---|---|---|
| 1* | 12.836 | 11.678 | 1.51633 | 64.1 |
| 2 | INFINITY | — | | |

Aspherical Surface Data

| NO | K | A4 | A6 | A8 |
|---|---|---|---|---|
| 1 | −1.000 | 0.2194E−04 | 0.2738E−07 | −0.3582E−11 |

| A10 | A11 |
|---|---|
| 0.0000E+00 | 0.0000E+00 |

Various Data

| Bf | 17.9 |
|---|---|
| Phi | 23.2 |
| NA1 | 0.56 |

In Table 1 (surface data), "NO" denotes the surface number. The surface number NO is assigned sequentially from a surface disposed on the light source 252 side. In Table 1 (surface data), "R" denotes a curvature radius (unit: mm) of each surface of an optical element constituting the collecting optical system 254, "D" denotes a thickness (unit: mm) of each optical element or an arrangement interval (unit: mm) of optical elements, "N(D)" denotes a refractive index of each optical element at d-line, and "VD" denotes Abbe number of each optical element at d-line. A surface having the surface number marked with an asterisk "*" is an aspherical surface. It should be noted that the curvature radius R defined for an aspherical element represents a curvature radius (a paraxial curvature radius) defined on an optical axis.

Table 1 (aspherical surface data) shows a shape (an aspherical shape) of a lens surface of the surface number 1. A shape of an aspherical surface is expressed by a following equation:

$$x = cy^2/[1+[1-(1+K)c^2y^2]^{1/2}] + A4y^4 + A6y^6 + A8y^8 + A10y^{10} + A12y^{12} \ldots$$

where, a sag amount is defined as "x", a curvature (1/r) is defined as "c", a height from the optical axis is defined as "y" (unit: mm), a conical coefficient is defined as "K" and aspherical coefficients larger than or equal to the fourth order are defined as A4, A6 . . . .

Table 1 (various data) shows the distance 131 (unit: mm) from a lens surface closest to the light guide rod 256 in the collecting optical system 254 to the entrance port 256a, the effective diameter (the diameter) "phi" of each lens surface, and the numerical aperture NA1.

The light guide rod 256 according to the example 1 has the partial taper configuration, and the concrete numeric configuration thereof is as follows.

$D_{EN}$: 8.0
$D_{EX}$: 5.0
L: 50

The example 1 supposes that the diameter (a diameter of an entrance port) $D_L$ of the entrance end face 17a of the LCB 17 of the electronic scope 100 to be connected to the light source device 250 is 2.9 mm.

Example 2

Figure 4:
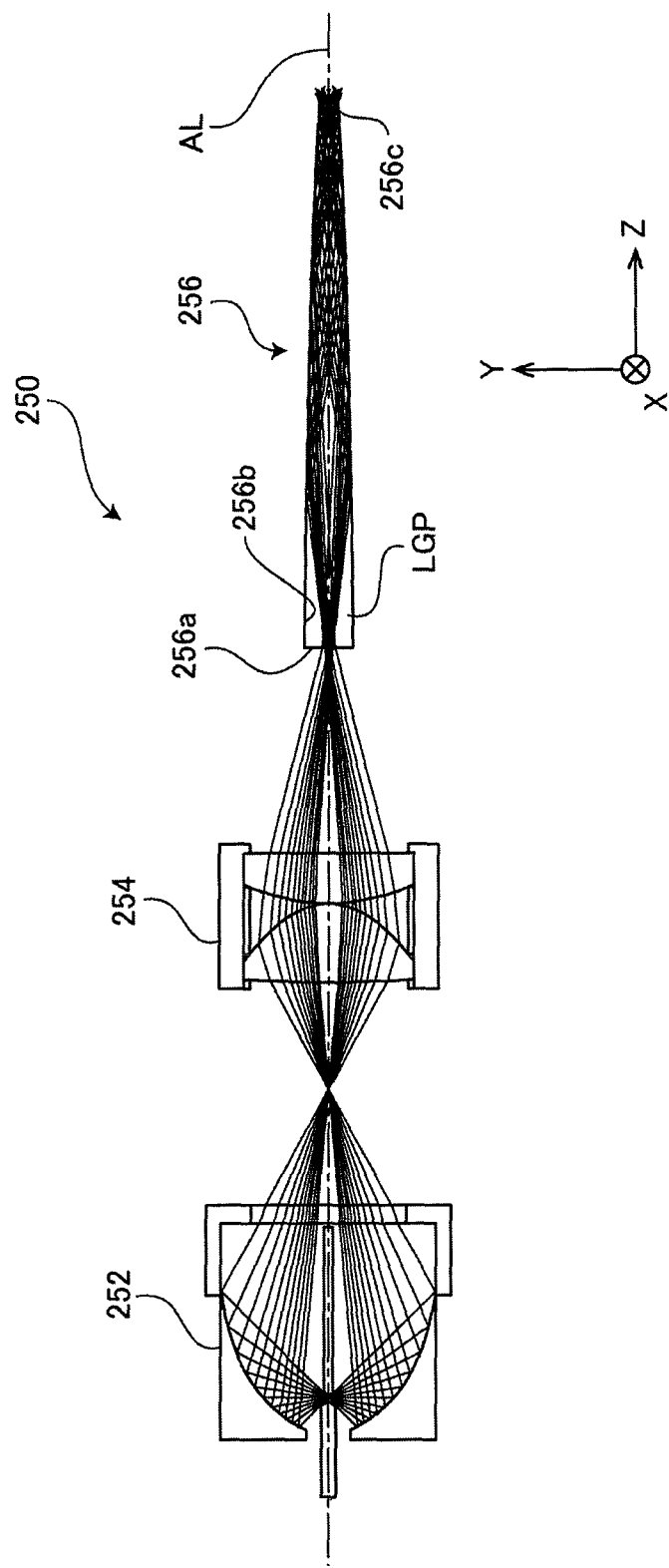
FIG. 4 illustrates a configuration of a light source device according to an example 2 of the invention.

FIG. 4 illustrates a configuration of the light source device 250 according to an example 2 of the invention. As shown in FIG. 4, in the example 2, the collecting optical system 254 has two lenses. The numeric Table 2 described below shows concrete numeric data of the collecting optical system 254 according to the example 2.

TABLE 2

Unit: mm

Surface Data

| NO | R | D | N(D) | VD |
|---|---|---|---|---|
| 1 | 180.00 | 13.043 | 1.52288 | 58.6 |
| 2* | −10.102 | 1.000 | | |
| 3 | 34.000 | 8.231 | 1.51633 | 64.1 |
| 4 | INFINITY | — | | |

Aspherical Surface Data

| NO | K | A4 | A6 | A8 |
|---|---|---|---|---|
| 2 | −1.000 | 0.9235E−05 | −0.8458E−07 | 0.3480E−09 |

| A10 | A12 |
|---|---|
| −0.8229E−12 | 0.0000E+00 |

Various Data

| Bf | 34.0 |
|---|---|
| Phi | 22.0 |
| NAI | 0.33 |

The light guide rod 256 according to the example 2 has the overall taper configuration, and the concrete numeric configuration thereof is as follows.

$D_{EN}$: 8.0

$D_{EX}$: 3.0

L: 90

The example 2 supposes that the diameter (a diameter of an entrance port) $D_L$ of the entrance end face 17a of the LCB 17 of the electronic scope 100 to be connected to the light source device 250 according to the example 2 is 2.9 mm.

Example 3

Figure 5:
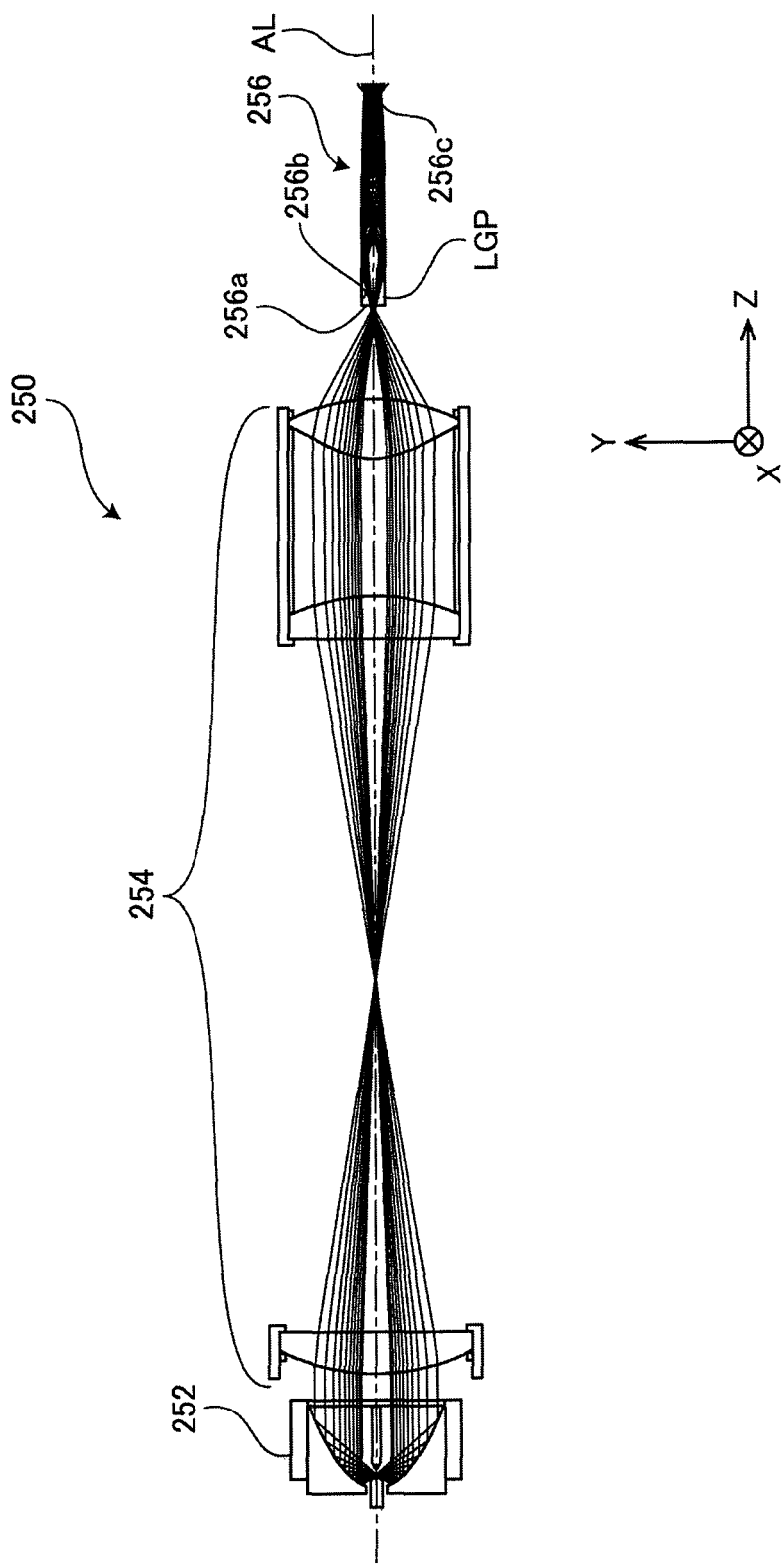
FIG. 5 illustrates a configuration of a light source device according to an example 3 of the invention.

FIG. 5 illustrates a configuration of the light source device 250 according to an example 3 of the invention. As shown in FIG. 5, in the example 3, the collecting optical system 254 has three lenses. The numeric Table 3 described below shows concrete numeric data of the collecting optical system 254 according to the example 3.

TABLE 3

Unit: mm

Surface Data

| NO | R | D | N(D) | VD |
|---|---|---|---|---|
| 1 | 37.951 | 8.087 | 1.51633 | 64.1 |
| 2 | INFINITY | 130.994 | | |
| 3 | INFINITY | 8.087 | 1.51633 | 64.1 |
| 4 | −37.951 | 25.877 | | |
| 5* | 14.128 | 11.476 | 1.52288 | 58.6 |
| 6 | −33.919 | — | | |

TABLE 3-continued

Unit: mm

Aspherical Surface Data

| NO | K | A4 | A6 | A8 |
|---|---|---|---|---|
| 5 | −1.000 | −0.1884E−04 | −0.1161E−06 | −0.8146E−10 |

| A10 | A12 |
|---|---|
| 0.8308E−12 | 0.0000E+00 |

Various Data

| Bf | 17.5 |
|---|---|
| Phi | 25.1 |
| NAI | 0.63 |

The light guide rod 256 according to the example 3 has the overall taper configuration, and the concrete numeric configuration thereof is as follows.

$D_{EN}$: 4.5

$D_{EX}$: 3.0

L: 40

The example 3 supposes that the diameter (a diameter of an entrance port) $D_L$ of the entrance end face 17a of the LCB 17 of the electronic scope 100 to be connected to the light source device 250 according to the example 3 is 2.9 mm.

Example 4

Figure 6:
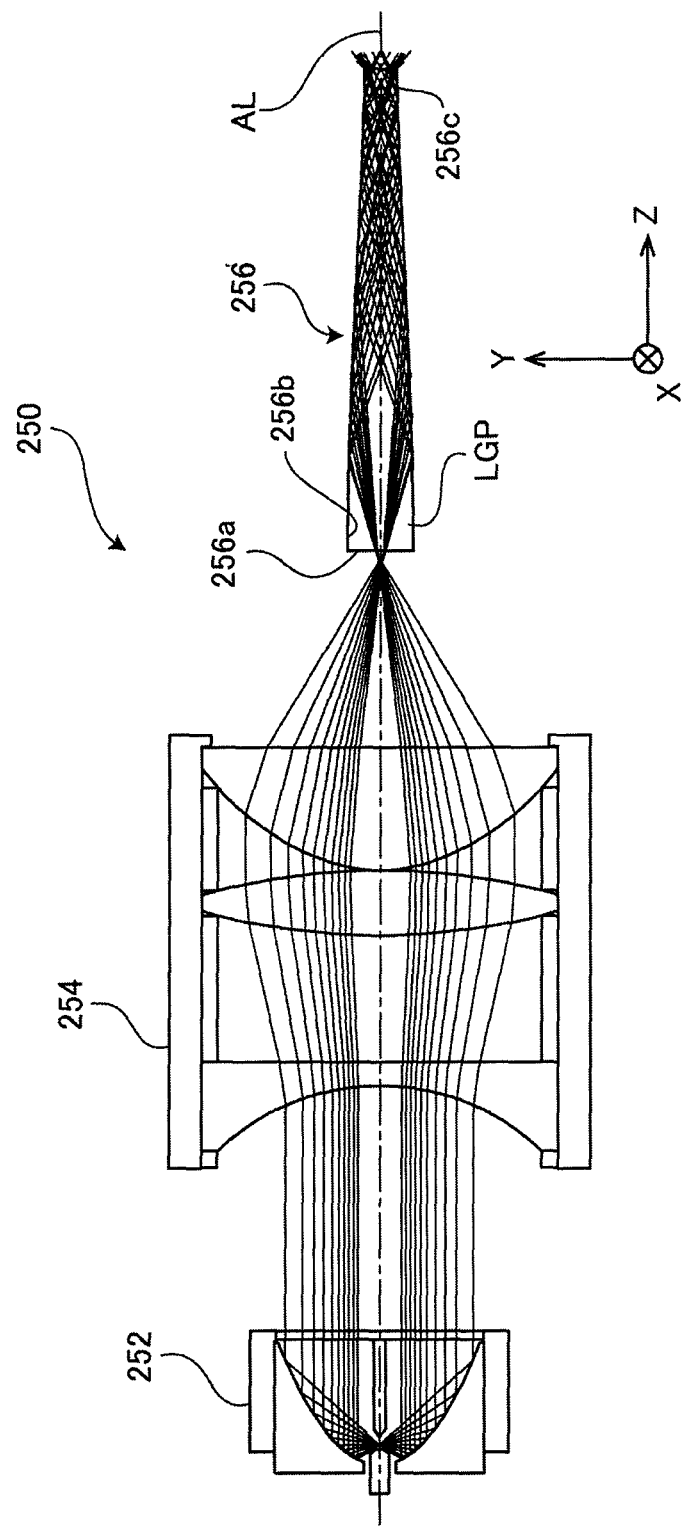
FIG. 6 illustrates a configuration of a light source device according to an example 4 of the invention.

FIG. 6 illustrates a configuration of the light source device 250 according to an example 4 of the invention. As shown in FIG. 6, in the example 4, the collecting optical system 254 has three lenses. The numeric Table 4 described below shows concrete numeric data of the collecting optical system 254 according to the example 4.

TABLE 4

Unit: mm

Surface Data

| NO | R | D | N(D) | VD |
|---|---|---|---|---|
| 1 | −28.720 | 3.000 | 1.51742 | 52.4 |
| 2 | INFINITY | 15.713 | | |
| 3 | 81.280 | 8.145 | 1.51633 | 64.1 |
| 4 | −81.280 | 0.100 | | |
| 5* | 20.073 | 15.231 | 1.66910 | 55.4 |
| 6 | INFINITY | — | | |

Aspherical Surface Data

| NO | K | A4 | A6 | A8 |
|---|---|---|---|---|
| 5 | −1.000 | −0.8538E−06 | 0.1254E−07 | −0.1396E−10 |

| A10 | A12 |
|---|---|
| 0.0000E+00 | 0.0000E+00 |

Various Data

| Bf | 24.4 |
|---|---|
| Phi | 34.7 |
| NAI | 0.63 |

The light guide rod 256 according to the example 4 has the overall taper configuration, and the concrete numeric configuration thereof is as follows.

$D_{EN}$: 8.2
$D_{EX}$: 4.2
L: 60

The example 4 supposes that the diameter (a diameter of an entrance port) $D_L$ of the entrance end face 17a of the LCB 17 of the electronic scope 100 to be connected to the light source device 250 according to the example 4 is 4.1 mm.

Example 5

Figure 7:
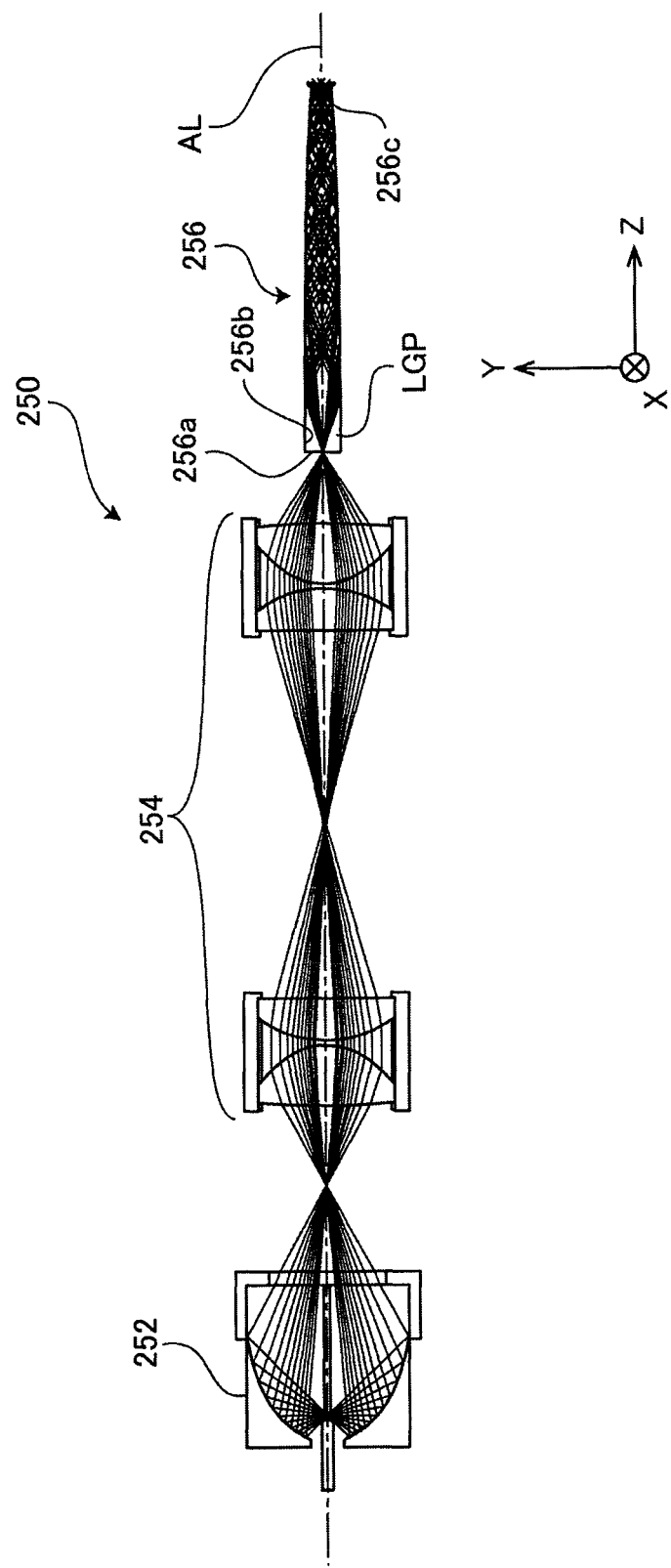
FIG. 7 illustrates a configuration of a light source device according to an example 5 of the invention.

FIG. 7 illustrates a configuration of the light source device 250 according to an example 5 of the invention. As shown in FIG. 7, in the example 5, the collecting optical system 254 has four lenses. The numeric Table 5 described below shows concrete numeric data of the collecting optical system 254 according to the example 5.

TABLE 5

Unit: mm

Surface Data

| NO | R | D | N(D) | VD |
|---|---|---|---|---|
| 1 | 160.000 | 13.427 | 1.52288 | 58.6 |
| 2* | −13.130 | 1.000 | | |
| 3 | 24.522 | 9.387 | 1.51633 | 64.1 |
| 4 | INFINITY | 80.889 | | |
| 5 | INFINITY | 9.387 | 1.51633 | 64.1 |
| 6 | −24.522 | 1.000 | | |
| 7* | 13.130 | 13.427 | 1.52288 | 58.6 |
| 8 | −160.000 | — | | |

Aspherical Surface Data

| NO | K | A4 | A6 | A8 |
|---|---|---|---|---|
| 2 | −1.000 | −0.5239E−05 | −0.2030E−07 | 0.1088E−09 |

| A10 | A12 |
|---|---|
| −0.1664E−12 | 0.0000E+00 |

| NO | K | A4 | A6 | A8 |
|---|---|---|---|---|
| 7 | −1.000 | 0.5239E−05 | 0.2030E−07 | −0.1088E−09 |

| A10 | A12 |
|---|---|
| 0.1664E−12 | 0.0000E+00 |

Various Data

| Bf | 15.8 |
|---|---|
| Phi | 8.5 |
| NAI | 0.56 |

The light guide rod 256 according to the example 5 has the partial taper configuration, and the concrete numeric configuration thereof is as follows.
$D_{EN}$: 8.0
$D_{EX}$: 5.0
L: 80

The example 5 supposes that the diameter (a diameter of an entrance port) $D_L$ of the entrance end face 17a of the LCB 17 of the electronic scope 100 to be connected to the light source device 250 according to the example 5 is 4.0 mm.

Example 6

Figure 8:
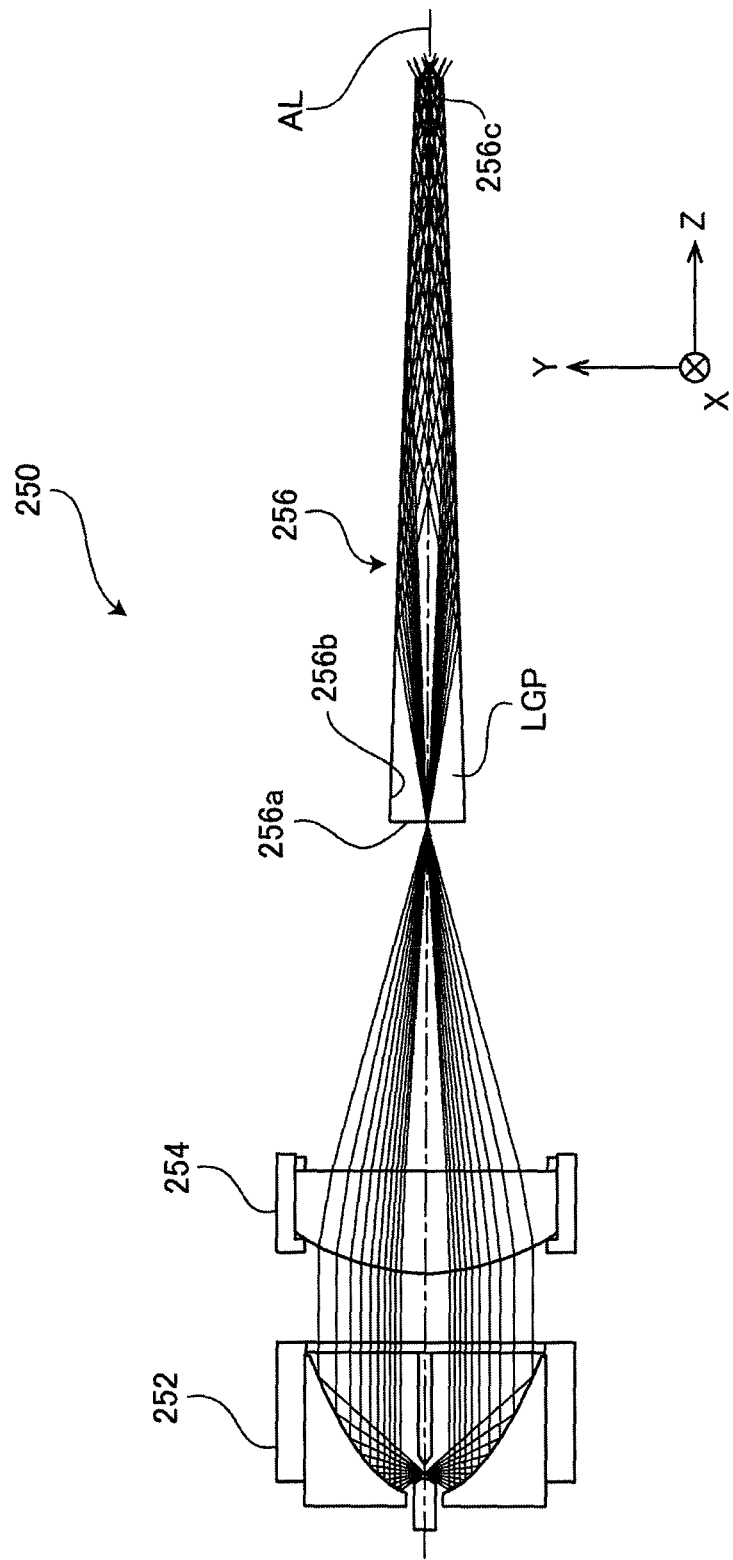
FIG. 8 illustrates a configuration of a light source device according to an example 6 of the invention.

FIG. 8 illustrates a configuration of the light source device 250 according to an example 6 of the invention. As shown in FIG. 8, in the example 6, the collecting optical system 254 has a single lens configuration. The numeric Table 6 described below shows concrete numeric data of the collecting optical system 254 according to the example 6.

TABLE 6

Unit: mm

Surface Data

| NO | R | D | N(D) | VD |
|---|---|---|---|---|
| 1* | 22.710 | 11.000 | 1.51633 | 64.1 |
| 2 | INFINITY | — | | |

Aspherical Surface Data

| NO | K | A4 | A6 | A8 |
|---|---|---|---|---|
| 1* | −1.000 | 0.2997E−05 | 0.1233E−08 | −0.5939E−11 |

| A10 | A12 |
|---|---|
| 0.0000E+00 | 0.0000E+00 |

Various Data

| Bf | 37.6 |
|---|---|
| Phi | 11.8 |
| NAI | 0.29 |

The light guide rod 256 according to the example 6 has the overall taper configuration, and the concrete numeric configuration thereof is as follows.
$D_{EN}$: 8.0
$D_{EX}$: 3.0
L: 80

The example 6 supposes that the diameter (a diameter of an entrance port) $D_L$ of the entrance end face 17a of the LCB 17 of the electronic scope 100 to be connected to the light source device 250 according to the example 6 is 2.9 mm.

Example 7

Figure 9:
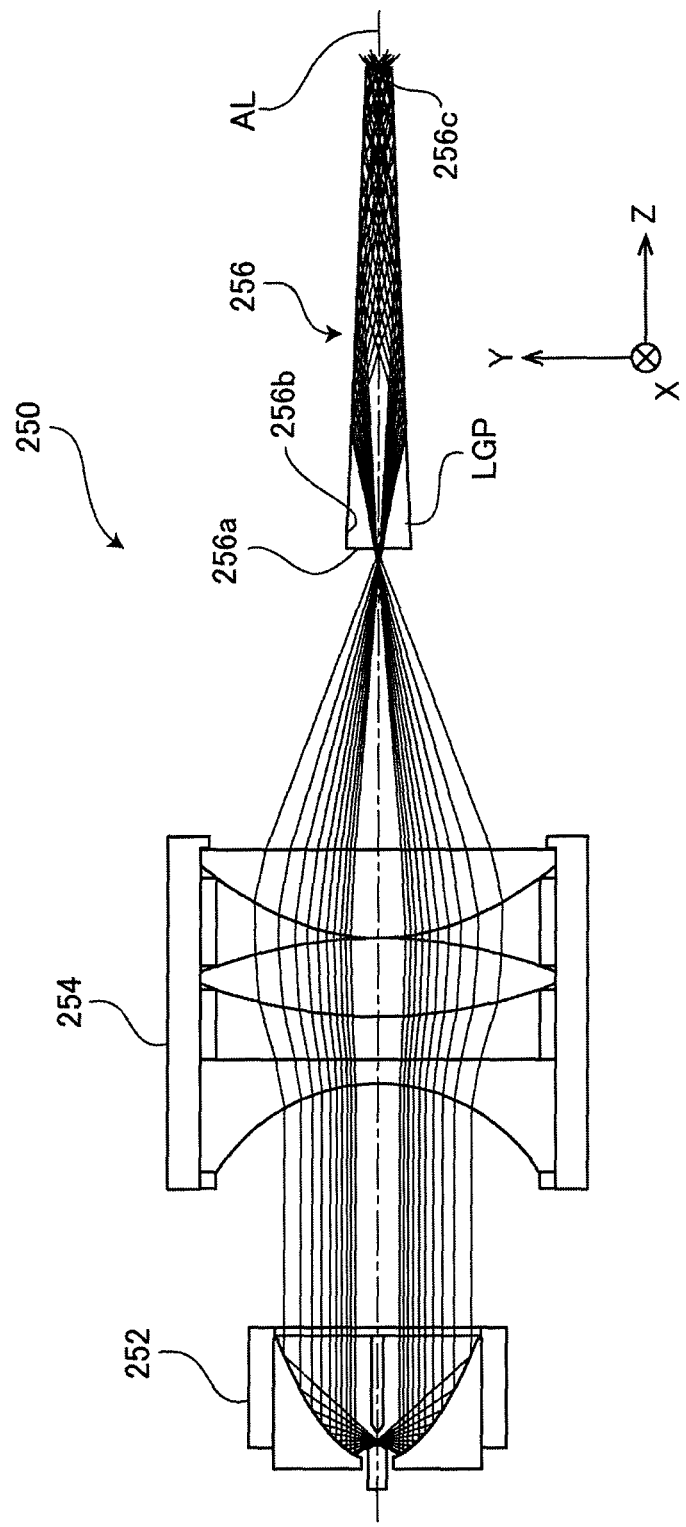
FIG. 9 illustrates a configuration of a light source device according to an example 7 of the invention.

FIG. 9 illustrates a configuration of the light source device 250 according to an example 7 of the invention. As shown in FIG. 9, in the example 7, the collecting optical system 254 has three lenses. The numeric Table 7 described below shows concrete numeric data of the collecting optical system 254 according to the example 7.

TABLE 7

Unit: mm

Surface Data

| NO | R | D | N(D) | VD |
|---|---|---|---|---|
| 1 | −23.495 | 3.000 | 1.51742 | 52.4 |
| 2 | INFINITY | 5.346 | | |
| 3 | 60.720 | 9.674 | 1.51633 | 64.1 |
| 4 | −60.720 | 0.100 | | |
| 5* | 25.409 | 11.114 | 1.66910 | 55.4 |
| 6 | INFINITY | — | | |

Aspherical Surface Data

| NO | K | A4 | A6 | A8 |
|---|---|---|---|---|
| 5 | −1.000 | −0.2467E−05 | 0.1020E−08 | −0.2235E−11 |

| A10 | A12 |
|---|---|
| 0.0000E+00 | 0.0000E+00 |

TABLE 7-continued

Unit: mm

Various Data

| | |
|---|---|
| Bf | 37.3 |
| Phi | 16.0 |
| NA1 | 0.42 |

The light guide rod 256 according to the example 7 has the overall taper configuration, and the concrete numeric configuration thereof is as follows.

$D_{EN}$: 8.0
$D_{EX}$: 3.0
L: 60

The example 7 supposes that the diameter (a diameter of an entrance port) $D_L$ of the entrance end face 17a of the LCB 17 of the electronic scope 100 to be connected to the light source device 250 according to the example 7 is 2.9 mm.

(Verification)

Table 8 described below shows a list of results obtained by applying the above described conditions (1) to (7) to the light source devices 250 according to the examples 1 to 7 (Ex. 1 to Ex. 7). As shown in Table 8, each of the light source devices 250 according to the examples 1 to 7 satisfies the conditions (1) to (5) and (7). Regarding the light source devices 250 according to the examples 1, 3 and 4, the condition (6) is also satisfied. Therefore, in each of the examples 1 to 7, the above described advantageous effects achieved by satisfying the respective conditions are also achieved.

TABLE 8

| | EX. 1 | EX. 2 | EX. 3 | EX. 4 | EX. 5 | EX. 6 | EX. 7 |
|---|---|---|---|---|---|---|---|
| CONDITION (1) | 1.60 | 2.67 | 1.50 | 1.95 | 1.60 | 2.67 | 2.67 |
| CONDITION (2) | 0.16 | 0.09 | 0.11 | 0.14 | 0.10 | 0.10 | 0.13 |
| CONDITION (3) | 31.25 | 33.75 | 26.67 | 30.73 | 50.00 | 30.00 | 22.50 |
| CONDITION (4) | 1562.50 | 3037.50 | 1066.67 | 1843.90 | 4000.00 | 2400.00 | 1350.00 |
| CONDITION (5) | 0.89 | 0.89 | 0.94 | 1.22 | 0.89 | 0.78 | 1.11 |
| CONDITION (6) | 1.24 | 4.11 | 1.05 | 1.37 | 2.99 | 8.51 | 6.22 |
| CONDITION (7) | Satisfied | Satisfied | Satisfied | Satisfied | Satisfied | Satisfied | Satisfied |

The foregoing is the explanation about the embodiment of the invention. The invention is not limited to the above described embodiment, but can be varied in various ways within the scope of the invention. For example, the invention includes a combination of embodiments explicitly described in this specification and embodiments easily realized from the above described embodiment.

In the above described embodiment, the light source device 250 is configured as a single device (a processor 200) integrated with components for executing image signal processing; however, the invention is not limited to such a configuration. For example, the light source device 250 may be configured as an individual device separately provided from the components for executing image signal processing.

In the above described embodiment, the light source device 250 is configured as a light source device for an electronic scope; however, the invention is not limited to such a configuration. For example, the light source device 250 may be configured as a light source device for an optical fiber.

The invention claimed is:

1. A light source optical system, comprising:
   a collecting optical system configured to collect light incident on the collecting optical system from a light source, the collecting optical system having at least one lens;
   a light guide rod having a circular entrance port through which the light collected by the collecting optical system enters the light guide rod, an reflecting inner surface defining a light guide path for the light inputted through the entrance port, and a circular exit port through which the light guided in the light guide path by being totally reflected on the reflecting inner surface exits; and
   a light guide having an entrance end arranged to receive light emerging from the exit port of the light guide rod,
   wherein the reflecting inner surface includes a taper part formed in one of an entire region defined from the entrance port to the exit port and a part defined from a midway point between the entrance port and the exit port to the exit port, the taper part being inclined to gradually get closer to an axis line of the light guide path at a point closer to the exit port,
   wherein the collecting optical system is configured to converge the light incident on the collecting optical system from the light source proximate the entrance port of the light guide rod,
   wherein when a diameter of the entrance port is defined as $D_{EN}$ (unit: mm) and a diameter of the exit port is defined as $D_{EX}$ (unit: mm), the light guide rod satisfies a following condition:

$$1.5 \leq D_{EN}/D_{EX} \leq 3.0, \text{ and}$$

wherein when a diameter of the entrance end face of the light guide is defined as $D_L$ (unit: mm), the light guide rod satisfies a following condition:

$$D_L < D_{EX}.$$

2. The light source optical system according to claim 1,
   wherein when a numerical aperture of the collecting optical system is defined as NA1, the light source optical system satisfies a following condition:

$$0.7 \leq D_{EN}/D_{EX} \times NA1 \leq 1.5.$$

3. The light source optical system according to claim 1, wherein, when a distance between a lens surface closest to the light guide rod in the collecting optical system and the entrance port of the light guide rod is defined as Bf (unit: mm), an effective diameter of the lens surface is defined as phi (unit: mm), and (Bf/phi) is defined as NA2, the light source optical system satisfies a following condition:

$$0.7 \leq D_{EN}/D_{EX} \times NA2 \leq 1.5.$$

4. The light source optical system according to claim 1, wherein when a length of the taper part in a direction of the axis line is defined as L (unit: mm), the light guide rod satisfies a following condition:

$$0.03 \leq D_{EN}/L \leq 0.16.$$

5. The light source optical system according to claim 4, wherein the light guide rod satisfies a following condition:

$$10 \leq D_{EX}/D_{EN} \times L \leq 60.$$

6. The light source optical system according to claim 4, wherein the light guide rod satisfies a following condition:

$$1000 \leq D_{EX}/D_{EN} \times L^2 \leq 4000.$$

7. A light source device, comprising:
a light source configured to emit collimated light; and
a light source optical system comprising:
   a collecting optical system configured to collect light incident on the collecting optical system from a light source, the collecting optical system having at least one lens;
   a light guide rod having a circular entrance port through which the light collected by the collecting optical system enters the light guide rod, an reflecting inner surface defining a light guide path for the light inputted through the entrance port, and a circular exit port through which the light guided in the light guide path by being totally reflected on the reflecting inner surface exits; and a light guide having an entrance end arranged to receive light emerging from the exit port of the light guide rod, wherein:
   the reflecting inner surface includes a taper part formed in one of an entire region defined from the entrance port to the exit port and a part defined from a midway point between the entrance port and the exit port to the exit port, the taper part being inclined to gradually get closer to an axis line of the light guide path at a point closer to the exit port,
   the collecting optical system is configured to converge the light incident on the collecting optical system from the light source proximate the entrance port of the light guide rod,
   the collimated light emitted from the light source is incident on the light source optical system,
   when a diameter of the entrance port is defined as $D_{EN}$ (unit: mm) and a diameter of the exit port is defined as $D_{EX}$ (unit: mm), the light guide rod satisfies a following condition:

$$1.5 \leq D_{EN}/D_{EX} \leq 3.0, \text{ and}$$

when a diameter of the entrance end face of the light guide is defined as $D_L$ (unit: mm), the light guide rod satisfies a following condition:

$$D_L < D_{EX}.$$

* * * * *